United States Patent [19]

Campbell et al.

[11] Patent Number: 5,622,695
[45] Date of Patent: *Apr. 22, 1997

[54] ANATOMICAL AND BIOLOGICAL PRESERVATIVE AND METHOD

[75] Inventors: James W. Campbell; John L. Margrave, both of Houston, Tex.

[73] Assignee: EFH, Inc., Houston, Tex.

[ * ] Notice: The term of this patent shall not extend beyond the expiration date of Pat. No. 5,405,606.

[21] Appl. No.: 306,696

[22] Filed: Sep. 15, 1994

Related U.S. Application Data

[63] Continuation-in-part of Ser. No. 161,893, Dec. 3, 1993, Pat. No. 5,405,606.

[51] Int. Cl.$^6$ ............................................. A01N 1/00
[52] U.S. Cl. ........................ 424/75; 27/22.1; 27/22.2; 514/717; 252/407
[58] Field of Search ...................... 424/75, 3; 27/22.1, 27/22.2; 514/717; 252/106

[56] References Cited

U.S. PATENT DOCUMENTS

| | | | |
|---|---|---|---|
| 3,057,775 | 10/1962 | Rendon | 424/75 |
| 3,197,366 | 7/1965 | Cannon et al. | 424/75 |
| 3,249,502 | 5/1966 | Hayden | 424/75 |
| 3,264,182 | 8/1966 | Langner | 424/75 |
| 3,293,127 | 12/1966 | Beck | 424/75 |
| 3,573,082 | 3/1971 | Fremling | 424/75 |
| 3,852,418 | 12/1974 | Tucker, Jr. | 424/75 |
| 3,912,809 | 10/1975 | Rendon | 27/22.2 |
| 4,021,537 | 5/1977 | Saurino | 424/54 |
| 4,121,944 | 10/1978 | VanLandingham | 424/75 |
| 4,263,278 | 4/1981 | Saurino et al. | 424/75 |
| 4,404,181 | 9/1983 | Mauthner | 424/75 |
| 4,946,669 | 8/1990 | Siegfried et al. | 424/75 |
| 5,196,182 | 3/1993 | Ryan | 424/75 |
| 5,260,048 | 11/1993 | Ryan | 424/3 |
| 5,374,378 | 12/1994 | Lorentzen et al. | 252/380 |
| 5,384,125 | 1/1995 | Dipippo et al. | 424/443 |
| 5,496,858 | 3/1996 | Eggensperger | 252/106 |

FOREIGN PATENT DOCUMENTS 0264658  4/1988  European Pat. Off. .

OTHER PUBLICATIONS

PCT Search Report mailed March 29, 1995.
Schwartz, Dr. Arthur and Barbara Schwartz, *Pollution Prevention Through Use of a Formaldehyde–Free Biological Preservative*, Apr. 1994, Belle Mead, NJ.
Wineski, Lawrence E. and Arthur E. English, "Phenoxyethanol as a Nontoxic Preservative in the Dissection Laboratory", Acta Anat 1989: 136:155–158.
Bedino, James H., "Millenium/New Era–Champion's Third Generation of Embalming Chemicals", Champion Report, (no date).
Carolina Carosafe, "Preserved Animals", (no date).
Connecticut Valley, "Preserved Material", (no date).
Nebraska Scientific, "Quality Specimens", (no date).
Streck Tissue Fixative, Streck Laboratories, Inc., Oct. 1992.
Ward's, "Preserved Materials", (no date).
McKone, Harold T., "Embalming: A Rite Involving Early Chemistry", Todays Chemist at Work, Apr. 1994, pp. 68–70.
Champion, "Millenium New Era Crisine Ultra Brochure and Material Safety Data Sheet" dated Oct. 1993.
Bedino, James H., "Expanding Encyclopedia of Mortuary Practices" Number 613, 1992, pp. 2466 through 2469.
Champion, "Millenium New Era Cavity 48 and Material Safety Data Sheet", dated Oct. 1993.

*Primary Examiner*—Amy Hulina
*Attorney, Agent, or Firm*—Fish & Richardson P.C.

[57] ABSTRACT

An improved preserving fluid and method has been developed. The fluid is a mixture including glutaraldehyde, an aromatic ether of ethanol e.g. phenoxyethanol, at least one alcohol, and a polyhydric alcohol humectant. The formulation has no formaldehyde.

12 Claims, No Drawings

ANATOMICAL AND BIOLOGICAL PRESERVATIVE AND METHOD

RELATED APPLICATIONS

This application is a continuation-in-part of Ser. No. 08/161,893 filed Dec. 3, 1993 issued Apr. 11, 1995 U.S. Pat. No. 5,405,606 by James W. Campbell and John L. Margrave, which is wholly incorporated by reference herein Ser. No. 08/306,645, filed Sep. 15, 1994. A related application is being filed contemporaneously with this application entitled "Improved Embalming Composition and Method."

BACKGROUND OF THE INVENTION

Anatomical and biological preservatives typically used contained significant quantities of formaldehyde. The formaldehyde solutions fix the tissues of the specimen and preserve the specimen from decay. Many plant and animal species are preserved for academic study. Smaller life forms are immersed in a preservative. Larger vascular animals are injected in the circulatory system and elsewhere with a preservative. Although formaldehyde solutions have historically been the preservative fluid of choice, there are a number of drawbacks. Formaldehyde is associated with certain health and environmental risks. In the United States, worker exposure to formaldehyde is subject to regulation. Also, formaldehyde can cause problems with the specimen, because it dehydrates the tissue.

Alternative preservation fluids have been proposed including phenols, alcohols, and certain acid preparations. Other methods have included initially fixing the specimen in formaldehyde, rinsing the specimen and placing the specimen in another solution that does not include formaldehyde.

Human remains used for morbid anatomy study are included in the specimens needing preservation. The desire to eliminate exposure to formaldehyde has been examined by investigators involved in cadaver preservation. Wineski et al., "Phenoxyethanol as a Nontoxic Preservative in the Dissection Laboratory," *Acta Anat.* Vol. 136 pp. 155–158 (1989). The cadavers were embalmed by injection with about 24 liters of formaldehyde fluids. After embalming the cadavers were immersed or completely wrapped with cloth heavily soaked in phenoxyethanol. Exposure of workers to phenoxyethanol is preferable environmentally to formaldehyde. However, the success of the technique depended on good initial preparation of the cadavers with a formaldehyde fluid.

Other alternatives to formaldehyde include a formulation made with a 1,4-dioxane ring compound, U.S. Pat. No. 3,264,182; a process of pre-fixation with formaldehyde followed by preservation with glycols, U.S. Pat. No. 3,573,082; and solutions of starch glycerite for marine animals to preserve color, U.S. Pat. No. 4,121,944.

SUMMARY OF THE INVENTION

A new anatomical and preservative fluid capable for use for specimens that are immersed and injected with fluid in the vascular system has been developed. The fluid is a mixture of glutaraldehyde, at least one aromatic ether of ethanol preferably phenoxyethanol, at least one alcohol, and a humectant. The composition may be prepared as a concentrate or diluted with water to the desired concentration. The fluid may contain various additives conventionally used in preservatives, including a color additive, pH buffer, an antioxidant, and mixtures thereof. A biocide may also be added for additional cidal activity in addition to the fluid components to kill mold and other microbes when the specimen is going to be used for a prolonged time. The fluid exhibits excellent cidal activity for microbes such as viruses.

DETAILED DESCRIPTION OF THE INVENTION

The improved preservation fluid of the present invention is a unique mixture of glutaraldehyde, at least one aromatic ether of ethanol, at least one humectant, and at least one alcohol. Generally, the fluid is diluted with water prior to use. The fluid can be prepared in dilutions appropriate for whole specimen preservative and vascular injection.

The preferred formulation includes the following components by volume after dilution: glutaraldehyde from 3.5%, aromatic ether of ethanol preferably phenoxyethanol from about 1% to about 3%, humectant from about 1% to about 9%, and an alcohol from about 27% to about 37%; and made up with water to the desired concentration. A preferred humectant is a polyhydric alcohol or mixtures of more than one polyhydric alcohol. The preferred polyhydric alcohols are glycerol and 1,2 propanediol. Another polyhydric alcohol humectant is hexylene glycol. A preferred aromatic ether of ethanol is phenoxyethanol. The preferred components are not intended to limit the scope of the inventions and alternative components within the scope of the invention will be recognized by those skilled in the art.

The following Example 1 is an illustration of the improved composition that can be used for specimen preservation.

| Components | Percent by Volume |
| --- | --- |
| Ethyl Alcohol | 33% |
| Glutaraldehyde | 3% |
| 1-2 Propanediol | .7% |
| Phenoxyethanol | 2% |
| Glycerol | 3% |

The rest of the volume is made up with water. In addition, ethoxyethanol in the range of 0.5% to 0.9% by volume may be added to Example 1. Dimethyl sulfoxide may also be used preferably in the range of 0.5% to 1.0%. Ethanol is a preferred alcohol. Small amounts of isopropanol, methanol or mixtures thereof can be used as a denaturant or otherwise in the formulation.

In addition to the components in Example 1, a pH buffer preferably sodium phosphate and/or anti-oxidant may be included to maintain the stability of the glutaraldehyde. The pH buffer would adjust the pH in the range of pH~7 to pH~9 with the preferred range of pH 8.0–8.1. Also, a biocide may be added to further deter microbial growth. In addition, other additives conventionally used in preservation fluids such as color additives may be included. Color additives are used in vascular systems for identification. It is not intended to limit the claimed formulation to exclude additives known to be used in preservative compositions that would be compatible with the formulation of the present invention.

The improved composition includes glutaraldehyde in relatively small concentrations. Anatomical tissues treated with this fluid have exhibited good color retention in muscle tissue of cadavers. The specimens have no odor and are easy to work with. The more glutaraldehyde is used in the formulation the more rigid the joints will be of specimens with a skeletal structure.

The examples and methods described herein are not intended to limit the scope of the invention. Those skilled in the art will recognize variations and substitutions in the composition and method that fall within the scope of the invention.

We claim:

1. An anatomical and biological preservative fluid comprising glutaraldehyde in the amount of about 0.5% to about 3.5% by volume of the fluid;

phenoxyethanol in the amount of about 1% to about 3% by volume of the fluid;

alcohol in the amount of about 27% to about 37% by volume of fluid;

at least one polyhydric alcohol in the amount of about 1% to about 9% by volume of the fluid; and water.

2. A preservative fluid of claim 1 wherein said polyhydric alcohol is selected from the group consisting essentially of glycerol, 1-2 propanediol, hexylene glycol and mixtures thereof.

3. A preservative fluid of claim 1 additionally comprising a color additive.

4. A preservative fluid of claim 1 additionally comprising a pH buffer.

5. A preservative fluid of claim 1 additionally comprising an antioxidant.

6. A preservative fluid of claim 1 additionally comprising a biocide.

7. A preservative fluid of claim 1 additionally comprising dimethylsulfoxide from about 0.5% to about 1% by volume of the fluid.

8. A preservative fluid of claim 1 wherein said alcohol is ethanol.

9. A preservative fluid of claim 8 additionally comprising one of the group consisting of isopropanol, methanol and mixtures thereof.

10. A preservative fluid of claim 1 additionally comprising ethoxyethanol from about 0.5% to about 0.9%.

11. A method of anatomical and biological preserving, comprising:

preparing a fluid according to claim 1; and introducing a specimen into the fluid.

12. A method of preserving of claim 11 additionally comprising the step of introducing the fluid into the vascular system of the specimen.

* * * * *

UNITED STATES PATENT AND TRADEMARK OFFICE
CERTIFICATE OF CORRECTION

PATENT NO.  : 5,622,695

DATED       : April 22, 1997

INVENTOR(S) : James W. Campbell; John L. Margrave

It is certified that error appears in the above-identified patent and that said Letters Patent is hereby corrected as shown below:

In Column 2, Line 15 please insert after glutaraldehyde "from about 0.5% to about" before 3.5%.

Signed and Sealed this

Second Day of September, 1997

*Attest:*

BRUCE LEHMAN

*Attesting Officer*         Commissioner of Patents and Trademarks